(12) United States Patent
Ragless

(10) Patent No.: US 7,556,934 B2
(45) Date of Patent: Jul. 7, 2009

(54) CONCENTRATION MEASUREMENT BY SENSING HYDROGEL PRESSURE

(76) Inventor: Clive Lindsay Ragless, 5-11 Colley Terrace, Unit 26, Glenelg, South Australia (AU) 5045

( * ) Notice: Subject to any disclaimer, the term of this patent is extended or adjusted under 35 U.S.C. 154(b) by 150 days.

(21) Appl. No.: 10/491,249

(22) PCT Filed: Oct. 4, 2002

(86) PCT No.: PCT/AU02/01358

§ 371 (c)(1),
(2), (4) Date: Mar. 30, 2004

(87) PCT Pub. No.: WO03/031945

PCT Pub. Date: Apr. 17, 2003

(65) Prior Publication Data

US 2005/0003517 A1    Jan. 6, 2005

(30) Foreign Application Priority Data

Oct. 5, 2001    (AU) ................................... PR8080

(51) Int. Cl.
*C12Q 1/54* (2006.01)
*G01N 33/00* (2006.01)
*A01K 43/00* (2006.01)
*G01N 7/20* (2006.01)
*G01N 7/00* (2006.01)

(52) U.S. Cl. .................. 435/14; 422/82.13; 422/99; 436/94; 436/95; 426/231; 73/169

(58) Field of Classification Search .................. 436/94
See application file for complete search history.

(56) References Cited

U.S. PATENT DOCUMENTS 4,595,583 A * 6/1986 Eckenhoff et al. .......... 424/438

(Continued)

FOREIGN PATENT DOCUMENTS

EP    0313805 B1    5/1989

(Continued)

OTHER PUBLICATIONS

Han et al., Constant-Volume Hydrogel Osmometer: A New Device Concept for Miniature Biosensors, Jun. 7, 2002, ACS Publications, Biomacromolecules, vol. 3, pp. 1271-1275.*

(Continued)

*Primary Examiner*—Jill Warden
*Assistant Examiner*—Neil Turk
(74) *Attorney, Agent, or Firm*—R. Neil Sudol; Henry D. Coleman; William J. Sapone

(57) ABSTRACT

A sensor and method for measuring the concentration of one or more chemical substances within a solution. The sensor including a body of saturated hydrogel held within a sensor body. A window to allow flow through of the chemical substance to be measured. The hydrogel is held under a predetermined compressive force within the sensor body such that the hydrogel exerts a base pressure. A pressure sensor such as a strain gauge senses the pressure exerted by the hydrogel within the sensor body. The sensed pressure is stored or displayed. The hydrogel is reactive to the one or more chemical substances so that contact causes the hydrogel to either increase the pressure above the base pressure under which the hydrogel is held or to decrease the pressure relative to the base pressure of the hydrogel.

4 Claims, 3 Drawing Sheets

U.S. PATENT DOCUMENTS

| | | | |
|---|---|---|---|
| 5,054,882 | A | 10/1991 | Riccitelli et al. |
| 5,747,349 | A * | 5/1998 | van den Engh et al. ..... 436/172 |
| 6,264,612 | B1 | 7/2001 | McConnell et al. |
| 6,268,161 | B1 * | 7/2001 | Han et al. ..................... 435/14 |
| 6,268,405 | B1 * | 7/2001 | Yao et al. .................... 523/113 |
| 6,514,689 | B2 * | 2/2003 | Han et al. ...................... 435/4 |
| 2004/0248326 | A1 * | 12/2004 | Ziaie et al. .................... 438/1 |

FOREIGN PATENT DOCUMENTS

| | | |
|---|---|---|
| EP | 1076238 A2 | 2/2001 |
| SU | 705318 A | 12/1979 |
| WO | 99/17095 A1 | 4/1999 |
| WO | 00/37935 A1 | 6/2000 |
| WO | 01/16575 A1 | 3/2001 |
| WO | 01/81890 A2 | 11/2001 |
| WO | 02/19903 A1 | 3/2002 |
| WO | WO 03051286 A2 * | 6/2003 |

OTHER PUBLICATIONS

Swelling and Shrinking of Polyacid Gels; By A. Bensberg; 1997; pp. 323-340; *Continuum Mech. Thermodyn.*

Swelling, Elasticity and Structure of Hydrogels Prepaired vis bis-Macromonomers of Poly(ethylene oxide); By Sergey A. Dubrovskii, et al.; 2003; pp. 147-155; *Macromol. Symp.*

Water sorption of flexible networks based on 2-hydroxyethyl methacrylate-triethylenglycol dimethacrylate copolymers; By Carlos Peniche, Ms Eugenia Cohen, Blanca Vazquez & Julio San Roman; 1997 pp. 5997-5982; *Polymer* vol. 38, No. 24.

'Smart' polymers and what they could do in biotechnology and medicine.; By Igor Y. Galaev & Bo Mattiasson; 1999; pp. 335-340; *Tibtech.*

Environmentally Responsive Gels; By Stevin H. Gehrke & David C. Harsh; 1996; pp. 2093-2102; *CRC Press/University of Cincinatti/Dept. of Engineering.*

Effect of electrostatic interactions on phase transition in the swollen polymeric network; By Michal Iiavsky; 1981; pp. 1687-1691; *Institute of Macromolecular Chemistry, Czechoslovak Academy of Sciences.*

Catalase Effects on Glucose-Sensitive Hydrogels; By Dal-Young Jung, Jules J. Magda & In Suk Han; 2000; pp. 3332-3335; *M-Biotech Inc.*

Glucose Responsive Polymers (Medical Applications); By Joseph Kost; 1996; pp. 2825-2828; *CRC Press/Ben-Gurion University of the Negev.*

Glucose-sensitive membraines containing glucose oxidase: Activity, swelling & permeability studies: By Joseph Kost, Thomas A. Horbett, Buddy D. Ratner & Maninder Singh; 1985; pp. 1117-1133; *Journal of Biomedical Materials Research*, vol. 19.

A Revisibly Antigen-responsive Hydrogel; By Takashi Miyata, Noriko Asami & Tadashi Uragami; 1999; pp. 766-769; *Chemical Branch, Faculty of Engineering and High Technology Reasearch Center, Kansai University.*

Sensitive Glucose-Induced Change of the Lower Critical Solution Temperature of Poly [N,N-dimethylacrylamide-co-3-(acrylamido)phenyl-boronic acid] in Physiological Saline; By Kazunori Kataoka, Hiroaki Miyazaki, Teruo Okano & Yasuhisa Sakurai; 1994; pp. 1061-1062; *Macromolecules.*

Smart Hydrogels; By Kinam Park & Haeson Park; 1996; pp. 7785-7791; *CRC Press/Purdue University.*

Hydrophobic Weak Polyelectrolyte Gels: Studies of Swelling Equilibria & Kinetics; By Ronald A. Siegal; *Departments of Pharmacy and Pharmaceutical Chemistr, University of California, San Francisco* ; 1993.

Swelling of Ionic Gels in Electrolyte Solutions; By Ebrahim Vasheghani-Farahani, Juan H. Vera, David G. Cooper & Martin E. Weber; 1990; pp. 554-560; *American Chemical Society.*

* cited by examiner

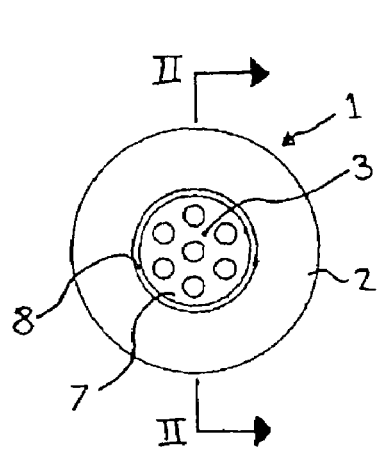
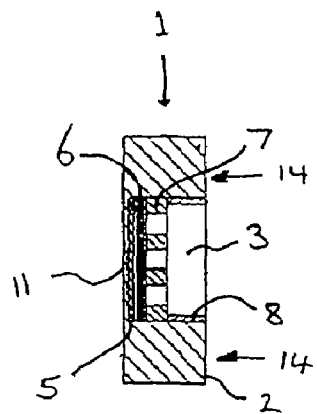
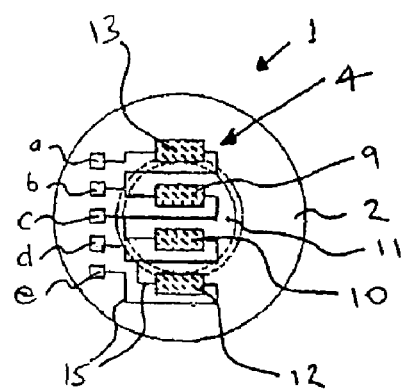
FIGURE 1    FIGURE 2    FIGURE 3
FIGURE 4
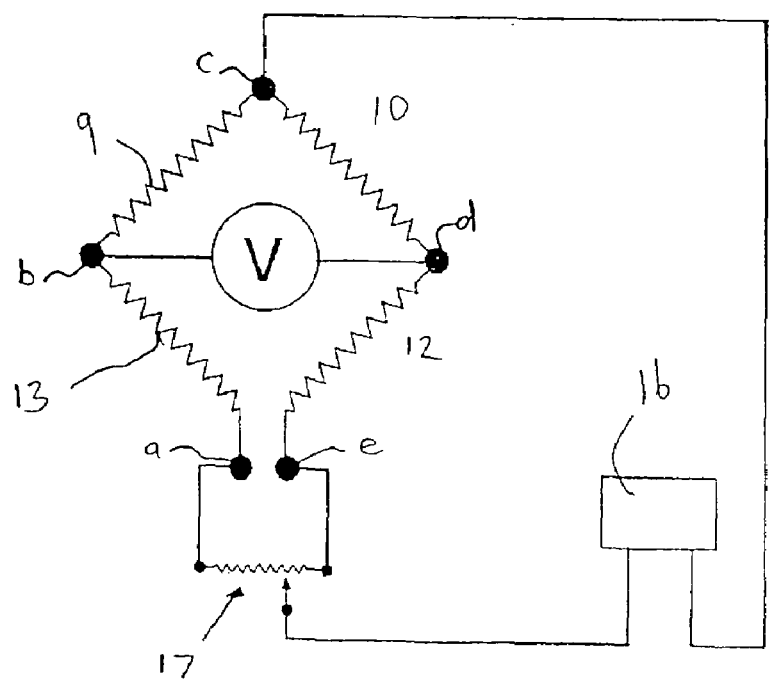

CONCENTRATION MEASUREMENT BY SENSING HYDROGEL PRESSURE

This invention relates to a method and apparatus for measuring the concentration of a chemical substance within a solution, and in one specific aspect the dynamic measurement of that concentration

BACKGROUND OF THE INVENTION

There are several circumstances where it is desired to measure the change in concentration of chemical substances in a solution in a dynamic fashion. In the wine making industry the levels of sugar and alcohol are measured in order to determine the extent to which the fermentation process should be continued. Similarly with the beer industry. Traditionally such industries measure the level of sugar by measuring the density of the solution by refractometry. Such a practice requires opening of the fermentation vat, with attendant risk of contamination, removing a sample and measuring. The method entails determining the refractive index of the solution which gives an indication of the density. A concordance table is consulted to determine the quantity of sugar. A calculation is then made to determine the reduction in sugar concentration relative to the starting concentration and from that a measure of the alcohol concentration is calculated. This calculated value gives only an approximation, requires the recordal of data manually and a direct sampling from the vat.

There have been suggested a number of approaches to measuring concentrations of various molecules, such as sugars in a dynamic fashion, and these include the use of an osmotic cell such as disclosed in U.S. Pat. No. 5,005,403 in the name of Steudle et al. This arrangement is quite complex and the document makes no disclosure of measuring the cumulative effects of multiple chemicals.

Another approach to measuring the presence of glucose is to use a specifically reactive, pH sensitive, hydrogel which has a glucose reactive linked enzyme the product of which reaction leads to changes in pressure emanating from the hydrogel. (see U.S. Pat. No. 6,268,161 to Han et al.,) This is a relatively complex arrangement suitable for specialised uses.

Hydrogels have been used in the past for monitoring. One such disclosure is WO 00/37935 by the present inventor whereby hydrogels held under a compressive force have been used to measure the matrix potential of soil.

OBJECT OF THE INVENTION

The object of the invention is to provide for a sensor that in a simple yet effective manner is able to determine the concentration of a chemical substance within a solution in a simple yet effective manner, or at least to provide the public with a useful alternative.

SUMMARY OF THE INVENTION

This invention arises from an arrangement whereby saturated hydrogel held under a predetermined pressure reacts to certain chemical moieties by increasing or decreasing the pressure in a manner directly, or inversely, related to the concentration of the chemical moiety concerned. This has been determined in particularly for sugar and alcohol which both are found to have effects on particular hydrogels held under pressure that are opposite in direction and quantitatively different so that this relationship can be used, in one specific form of the invention, in the wine industry. Other moieties also interact with hydrogels either singly or in combination and this invention therefore has broader applicability.

In a broad form of a first aspect this invention might be said to reside in a sensor for measuring the concentration of one or more chemical substances within a solution, said sensor including a body of saturated hydrogel held within a sensor body, said sensor body having at least a window to allow flow through of the one or more chemical substances to be measured, the hydrogel is held under a predetermined compressive force within the sensor body such that the hydrogel exerts a base pressure, the sensor further includes a pressure sensing means to sense the pressure exerted by the hydrogel within the sensor body, the pressure sensing means communicative with a storage or display means to store or display a sensed pressure, said hydrogel reactive to the one or more chemical substance which cause the hydrogel to either increase the pressure above the base pressure under which the hydrogel is held or to decrease the pressure relative to the base pressure of the hydrogel.

In an alternative broad form the invention could be said to reside in a method of monitoring the concentrations of one or more chemical substances in a solution said monitoring including the holding hydrogel under a predetermined pressure, exposing the hydrogel to the solution, recording the change in pressure in the hydrogel over time, the hydrogel chosen such that the one or more chemical substances exerts an expansive or a contractive effect on the hydrogel at the predetermined pressure applied to the hydrogel.

BRIEF DESCRIPTION OF THE DRAWINGS

FIG. 1 is a plan view from below of a first embodiment of a sensor, showing the body of the sensor and window for ingress of the solution, FIG. 2 is a cross sectional view through II-II of FIG. 1 showing detail of the manner in which a hydrogel is held in the body of the sensor by a porous ceramic disk which is further supported by a grate which defines the windows for ingress of the solution, the outside body of the sensor and a securing collar for securing the hydrogel and pressure transducer within the housing, FIG. 3 is a plan view from above showing the layout of piezo electric crystal overlaying the bridge of the body of the first embodiment of sensor, FIG. 4 is a layout of the manner in which the transducer functions and where the signals are processed.

DETAILED DESCRIPTION OF THE INVENTION

Figure 8:
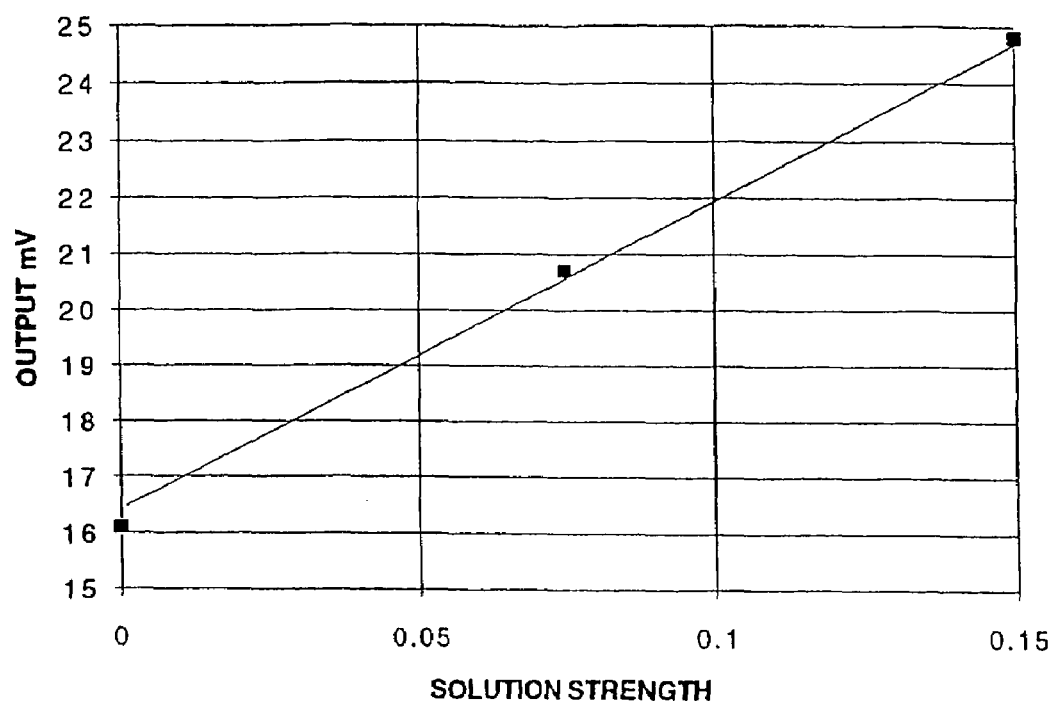
FIG. 8 is a graph of the output from the sensor with varying concentrations of alcohol.

The core of the sensor is a hydrogel that is held under a predetermined pressure. The compressive force leading to the pressure is to take the hydrogel to a state in which further changes in pressure in response to changes in concentration of certain chemical moieties has a predictable relationship. The pressure might be zero but preferably within a range from about 50 Kpa to about 400 kPa, more preferable between 100 and 300 kPa and most preferably about 200 Kpa. It is found that estimates of concentrations are more reliable when the hydrogel is held under a positive pressure, and in particular where exposure to any one of the chemical substances to be measured leads to a reduction in pressure by shrinkage of the hydrogel. The extent of the predetermined pressure might be such that it is sufficient to accommodate an anticipated decrease in pressure occasioned by measuring a range of concentrations of chemical substances causing reducing in pressure or shrinkage of the hydrogel.

Hydrogel are polymeric materials which swell in water and other solvents, absorbing fluid within the polymer network without dissolving. Hydrogels suitable for this invention are the expandable, driving swellable hydrophilic polymers, known as osmopolymers. The swellable hydrophilic polymers are cross-linked and may be lightly cross-linked, such cross-links being formed by covalent or ionic bond, which interact with water and aqueous biological fluids and swell or expand to some equilibrium state. The hydrogels can be of plant and animal origin, and may be prepared by modifying naturally occurring structures, and synthetic polymer hydrogels. The hydrogels exhibit considerable expansive capacity generally ranging from a 2 to 50 fold volume increase. Hydrogels useful for this invention may be selected from the following polymers, poly(hydroxyalkyl methacrylate), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methyl cellulose cross-linked with dialdehyde, a mixture of cross-linked agar and carboxymethyl cellulose, a water insoluble, water-swellable copolymer produced by forming a dispersion of finely divided copolymer of maleic anhydride with styrene, ethylene, propylene, butylene, or isobutylene cross-linked with from 0.001 to about 0.5 moles of a polyunsaturated cross-linked agent per mole of maleic anhydride in the copolymer, water-swellable polymers of N-vinyl lactams, cross-linked polyethylene oxides, and the like. Hydrogels are referred to in a number of US patent documents including the following U.S. Pat. Nos. 3,865,108, 4,022,173, 4,207,893 and in Handbook of Common Polymers by Scott and Roff, published by the Chemical Rubber Company, Cleveland, Ohio.

These hydrogels may be further modified to have specific or particular affinities for the one or more chemical substances the concentration of which is to be determined. Alternatively modification might be desired to repel or minimise the interaction of other compounds which would adversely impact on the reliability of the change in pressure.

The hydrogel will be selected to react with the chemical compound such that varying concentrations will either increase or decrease the pressure exerted by the hydrogel on the pressure sensor relative to the base pressure.

A hydroxyalkyl methacrylate hydrogel specifically a 2-hydroxyethyl methacrylate held at a base pressure of 200 kpa reacts with alcohol at levels relevant to wine and beer manufacture in an direct relationship with the concentration. The same hydroxyalkyl methacylate hydrogel is found to have an inverse relationship with sucrose, but quantitatively the relationship is different by a factor of about 3.2. As one might expect therefore, over time the fermentation of wine it was found that the pressure increases with time. The change in pressure exerted by the hydrogel over the course of wine fermentation might thus be expected to be a composite of the curves of the pressure changes exerted by a change in the concentration of sugar and the change in concentration of alcohol and other reactive substances in the fermentation vat. Trial conducted on wine fermentation show that using the above hydrogel that the change in pressure exerted by the hydrogel follows closely the curve in change in sugar concentration as measured by conventional techniques.

It is anticipated that in the case of dynamically measuring a fermentation process leading to the production of an alcohol from a simple or complex sugar that a range of hydrogels can be used, and these may be determined empirically. It is anticipated that certain hydrogels will have no or minimal reaction to the sugars fermented and will react primarily or solely to alcohol, and conversely other hydrogels will react primarily with the sugar concerned and minimally or not at all with alcohol. Candidate hydrogels can be tested for suitability by testing against varying concentrations of sugar and alcohol separately before being trialled in a fermentation.

From the above it will be understood that the hydrogel itself exerts the selectivity of reaction between two competing influences on pressure. It will be understood that other solutes may well also change and these are also likely to have an influence on the pressure exerted by the hydrogel. It is found with experimentation with wine and beer making that whatever other changes occur these are overshadowed by the change in concentration of sugar and alcohol, and that then gives a good measure of the extent to which fermentation has proceeded.

Whilst wine and beer making have been highlighted this finding will also be applicable to other fermentations that result in the production of alcoholic or industrial alcohols. Or indeed where alcohol is further modified such as in the production of vinegar where it might be desired to measure the decrease in the amount of alcohol in favour of vinegar. Alternative uses might be where the mixture of alcohol and another fluid might be measured to determine that the proportions are present in acceptable limits, perhaps in a supply line, after mixing of alcohol or other chemical substance in a solution.

In the alternative however it might be desired to provide a filter that precedes the hydrogel such that unwanted chemical moieties are excluded from contacting the hydrogel. Thus for example certain large molecular weight moieties might be excluded by providing for a molecular weight sieve to prevent direct interaction with the hydrogel.

It is to be understood that the solution need not necessarily be a solution of a single chemical substance, although the present invention might be applicable to determining the concentration of a pure solution, or alternatively where an entity is unstable, it might be used to plot the degradation of the chemical substance over time. Moreover whilst under the above, and other, circumstances it might be desirable to be able to provide an accurate estimate of the concentration of the chemical substance, a plot of the change in concentration may be equally useful, rather than simply providing an absolute value of concentration. Similarly in a more complex solution any plot in the change in pressure exerted by the hydrogel is likely to be a composite of the effects of two or more dominant species of chemical substance, and such a change can also be useful as a means of tracking the dynamic process such as a fermentation. Such tracking might determine when further reagent is to be added or further step is to be taken to, for example, stop the fermentation process.

Referring now to a first embodiment of the sensor (1) as shown in FIGS. 1 through to 3. The sensor body (2) takes the form of a disk shaped ceramic block. The sensor body includes a central bore (3) into which are placed a hydrogel disc (5), a permeable ceramic disc (6), and a perforated stainless steel disc (7). A retaining collar (8) also of stainless steel holds the above components in place in the bore.

The top of the sensor body includes components of a pressure transducer (4). Two piezo resistive strain gauges (9, 10) are positioned over a thin flexible ceramic membrane (11)

covering the bore of the sensor body, and the remaining two strain gauges (12, 13) are positioned over the annular portion (14) of the sensor body. Leads (for example at 15) are connected between the strain gauges and contacts (indicated as a to e) on the upper surface of the sensor body.

The sensor body and strain gauge arrangement used in this example are commercially available as a Metallux brand piezoresistive pressure transducer model ME 651ff with a sensitivity range from 0 to 500 Kpa. These are available from Metalux Electronics (Italy). In assembling the sensor, the hydrogel layer is inserted into the bore. The hydrogel takes the form of a 0.3 mm disk of 2 hydroxyethyl methacrylate sold under the Trade Mark Benz as G55 by Benz Research and Development (Florida, USA). G55 is used in the manufacture of optical contact lenses.

A block of 2 hydroxyethyl methacrylate is saturated with water, held and a cutting blade slices a desired thickness. The cut piece is positioned within the sensor body. The permeable ceramic disk is then positioned in place, being adhered to a thin disk of fibreglass to which is then adhered to the sensor body. The fibreglass assist with proper adhesion to the sensor body. Following that the perforated stainless steel disk (7) is put in place. The desired pressure is then applied to the perforated ceramic disk, in the present case this was 200 kPa, whilst the pressure is maintained a ceramic adhesive is applied, and the retaining collar is glued into place using for example and isocyanate adhesive. The pressure is applied until the adhesive sets at which time the pressure is released. In the alternative it might be desired to dry the cut piece of hydrogel, adhere the hydrogel to the sensor body, and allow an appropriate amount of room within the sensor body for expansion, to give the desired pressure when saturated within the body.

When placed in a 25% sugar solution with water, the pressure stabilised at a much lower level of about 100 Kpa, and when placed in an alcohol and water solution of 25% alcohol, the pressure stabilised at about 450 Kpa.

The dimensions of the sensor of the illustrated embodiment are as follows. 18 mm outside diameter, 9 mm inside diameter with a thickness of 6 mm. The permeable ceramic disk is kept as thin as possible to reduce lag time in measurement, and in the illustrated embodiment the permeable ceramic disk is a 0.5 mm thick piece of aluminium oxide. The holes within the grate are about 1.5 mm.

The general circuit for the sensor is shown in FIG. 4. The contacts labelled a to e can be seen on the diagram these are labelled in the same manner as in FIG. 3. A voltmeter (V) can be connected between contacts (b) and (d) to give a read out, or the voltage signal might be taken to a computer means for storage and or display. A power source (16) in the form of a battery is connected between contact (c) and (a) bridge adjusting potentiometer (17) which balances the potential difference between contacts (a) and (e).

It will be appreciated that as the pressure within the hydrogel changes, the ceramic membrane will flex and there will be a differential in signal between the two strain gauges (9, 10) on the membrane when compared with the two strain gauges (12, 13) that are positioned over the annular portion of the sensor body. This will alter the signal sent. This change in voltage can be stored and/or displayed on a computer, and can be used for comparisons with standards. It will be understood that a range of computational analysis of the voltage readout may be desirable.

Other forms of sensor arrangement can also be made. Strain gauge arrangements with multiple piezoresistors together with leads and contacts are often simply printed on one side of a ceramic wafer. One form of the present invention contemplates also printing on the reverse side a layer of appropriate hydrogel. It is anticipated that hydrogel compositions of this type will be available, the polymerisation of the hydrogel in this particular application may take placed in situ on the ceramic wafer. A wafer so formed could then be supported in a suitable sensor body. The invention in a further aspect might be said to reside in a wafer having strain gauges on one side and a hydrogel on an opposite side. The wafer might be a ceramic wafer or any other material suitable for use in detecting changes in pressure, by piezoresistive or other means.

Thus the thickness of the hydrogel can be quite thin. The experiment to date have been conducted on layers that have been cut to 0.3 mm dry thickness. Further reduction of this thickness has to date been limited by the machining techniques employed in the trials to date. It is anticipated that thinner layers will perform equally well, and layers of about 0.05 or 0.1 mm thickness might work equally well. The hydrogel disk is fastened, and sugar or alcohol have the effect of an increase in pressure resulting across the thickness of the disk and secondly by reason of an expansion radially. The thinness of the hydrogel is preferable because thinness leads to an enhanced reliability. However the invention could still quite readily be workable with a thicker hydrogel disk. Thus whilst the preferred embodiment contemplates thickness of about 0.5 mm or less hydrogel disks of perhaps 3 or 5 mm or more will also be quite adequate. Generally for reliability it is preferred that the thickness is less than 1 mm.

The role of the permeable ceramic disk is to hold the hydrogel firmly in place so that on a change in pressure an even pressure is exerted between the hydrogel and the surrounding sensor body and permeable ceramic disk. Where for example the hydrogel is to be mounted directly between the perforated ceramic disk and the bridge of the sensor body then there would be localised expansion of the hydrogel disk through the perforations. That would lead to an aberrant result.

Whilst the term disk is used in respect of the hydrogel body it might be desired to use differently shaped hydrogel bodies, and it might be desired to make the cross sectional shape non-circular, clearly these different shapes are also contemplated by the invention. Similarly the above description contemplates a unitary hydrogel piece, however multiple hydrogel particles may also be used. Thus in particular where the hydrogel is applied directly to a surface of strain gauge wafer as described above, particles of polymerised hydrogel might be applied within a permeable elastic settable material, the particles being of a size to facilitate the spraying or printed application of the hydrogel, and the settable material allowing for ready permeation of the solution to the hydrogel but being sufficiently elastic to allow pressure transmission resulting from the reaction of the hydrogel after contact with the solution. Alternatively segment of the hydrogel may be pieced together.

The sensor body might take any appropriate form where a ceramic wafer carries multiple piezoresistive element it will provide both a flexible portion and a rigid portion with for suitable positioning of the piezo resistive elements. Other pressure sensing means might also be provided for, and these might result from the use of the thicker hydrogel element that expands over a greater range to perceptible change. Other sensors might include those using piezoresistive elements in conjunction with a slicone membrane, and those that do not require piezoresistive elements such as copper/nickel or constantan based strain gauges.

Figure 5:
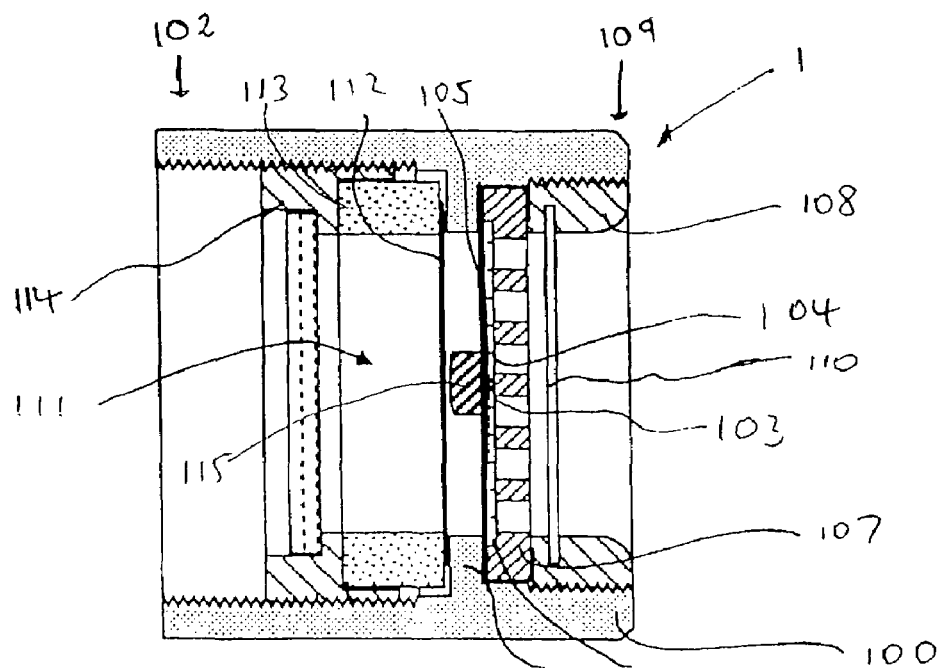
FIG. 5 is a similar cross sectional view of a second embodiment of a sensor according to the present invention.

A second embodiment of the sensor is shown in cross section in FIG. 5. The sensor (1) is intended to be screw-threaded to the end of a probe that might, for example, extend into a fermentation vat. A sensor housing (100) is made of stainless steel and is generally in the form of a sleeve apart from an inwardly extending flange (101) an upper portion (102) of the sensor housing is internally screw threaded for attachment to the probe. A lower portion of the sensor is open for contact with the test solution. The hydrogel disk is (103) is bonded to a thin ceramic disc (104). The hydrogel is generally thicker in the centre and tapers radially and is held within a cavity in the ceramic disc. The ceramic disc is approximately 0.5 mm and the thickest portion of the hydrogel is about 0.2 mm thick. It is found that convenient way to shape the hydrogel disk is to form a concave hollow in one surface of the ceramic disc, place a thin layer of saturated hydrogel over the concave hollow and apply a moderate pressure allowing the hydrogel to dry. It has been discovered that in doing so the hydrogel bonds to the ceramic disc. The hydrogel can then be finished to the surface of the ceramic disc thus ending up just filling the concave hollow. The hydrogel used in this embodiment is 2-hydroxyethyl methacrylate.

A spring disc (105) is placed against a lower surface of the flange (101). The combination of the ceramic disk and hydrogel is positioned into a recess (106) in a perforated stainless steel disc (107). A threaded retaining collar (108) is inserted threaded into the lower portion (109) of the sensor housing to retain the hydrogel assembly in place. It can be seen that the retaining collar has a circumferential flexing slot (110) formed therein to provide for some tension against the hydrogel assembly. A strain gauge (111) is positioned against the upstream face of flange (101). The construction of the strain gauge is very similar to that described in the first embodiment of the invention, in that a ceramic disc (112) is positioned over an annular ceramic support (113). Four strain gauges are positioned in a manner similar to that shown in FIG. 3. The strain gauge is retained in the upper portion of the sensor housing (100) by a strain gauge retaining collar (114) which is threaded into the housing and fastens the strain gauge in place. Spring disc (105) is in direct contact with the hydrogel, and is made of stainless steel, additionally it has a feature of a contact boss (115). The position of the contact boss is shown in FIG. 5 is where the hydrogel is in its dry state, where the boss is slightly spaced apart from the strain gauge. On wetting the hydrogel swells, influences the spring disc and attached contact boss to move toward the strain gauge and make contact therewith. The swelling of the hydrogel is constrained by the spring disc, which exerts pressure thereon. It will be appreciated that the shape of the hydrogel is shaped so as to exert an appropriate expansion of the disk, whereby a radially central portion bows further than circumferential portions.

The output of the second embodiment of the probe together with the arrangement described in FIG. 4 was then used to measure a number of test solutions, which were made up as either weight/volume solutions or volume/volume solutions. It can be seen that direct or indirect relationships are found with concentration of NaCl, sucrose and alcohol (methanol).

Figure 6:
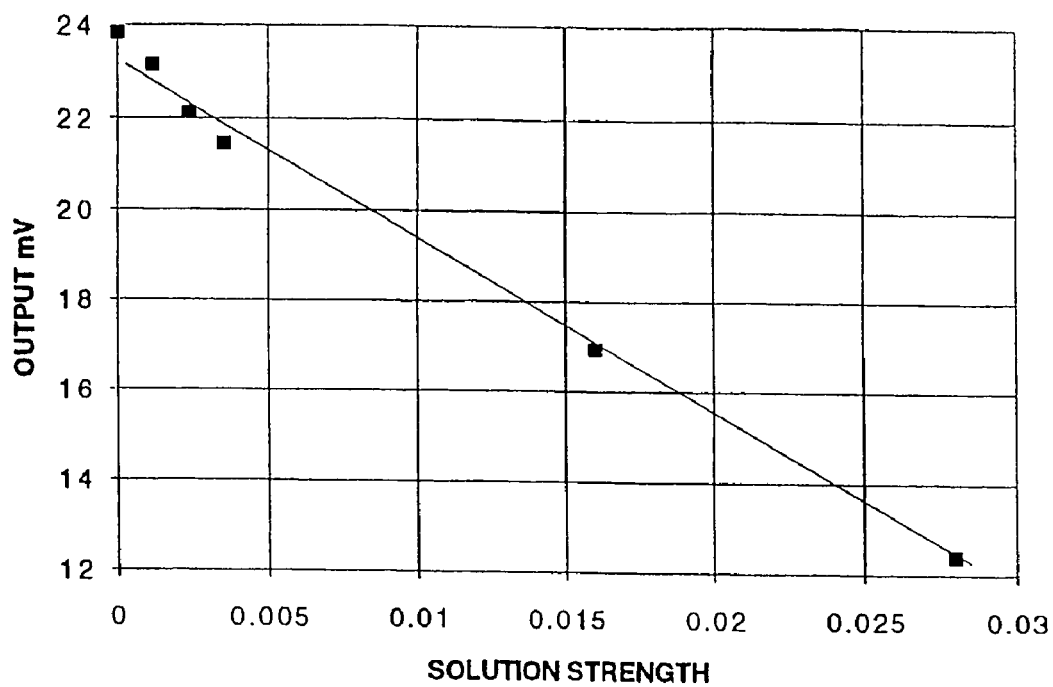
FIG. 6 is a graph of the output from the sensor with varying concentrations of sodium chloride.
Figure 7:
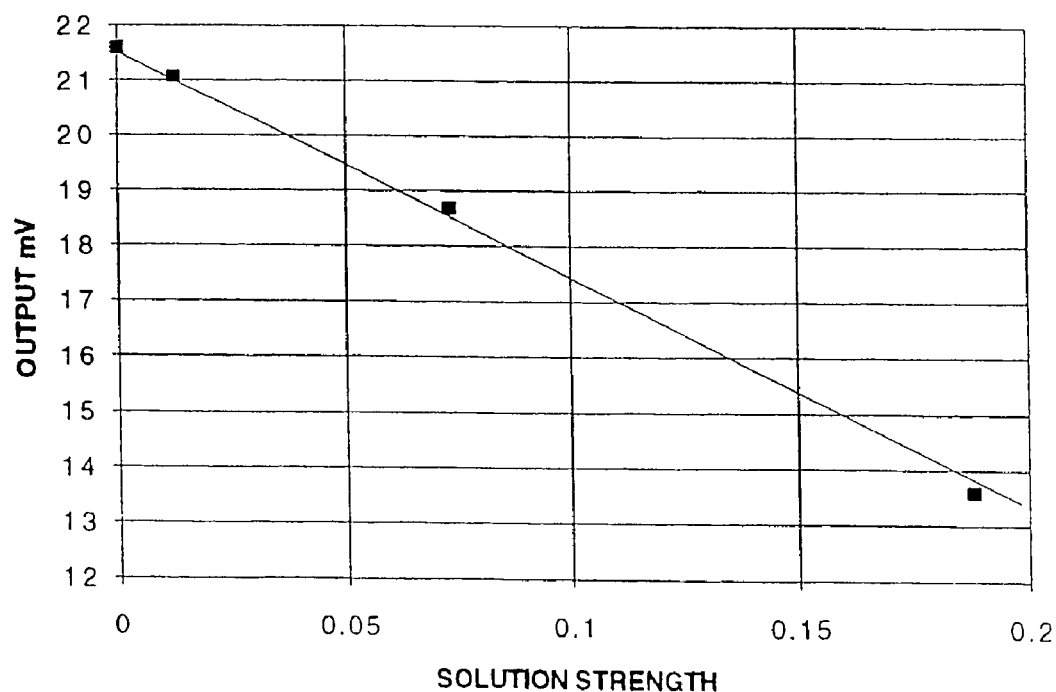
FIG. 7 is a graph of the output from the sensor with varying concentrations of sugar.

See FIGS. 6, 7 and 8 respectively. This shows the very good correlation in concentration within at least certain ranges.

In these examples the alcohol may act directly on the hydrogel through an interaction with the hydrogel structure to exert an expansion effect. The expansion effect thus is not by reason of drawing water out but rather perhaps by a replacement of water with alcohol or of further interaction with alcohol in addition to water. The sugar in the other hand exerts an osmotic effect reducing the amount of water within the hydrogel to cause a shrinkage, or reduction in pressure.

The second embodiment of the probe was also tested during wine making. It is found that over the weeks of a wine fermentation that the change in pressure output can be tracked and appears to follow estimates of sugar content quite closely. This trial thus shows that the other chemical substances in the complex wine making process do not adversely affect the capacity to track the changes that are important to winemaking. Given that trials with alcohol and sugar show that the reaction to sugar is a several times greater than that for the opposite reaction to alcohol it is not surprising that change in sugar in particular was closely tracked as opposed to changes in alcohol.

It is anticipated that a similar finding will be made with other fermentations where a change in sugar is tracked such as beer making, or where change in an alcohol is tracked such as in perhaps vinegar manufacture.

The invention claimed is:

1. A method of monitoring a wine or beer fermentation solution in a fermentation vessel, comprising:
    holding a saturated hydrogel under a base pressure of at least 50 kPA;
    exposing the hydrogel to the solution; and
    recording changes in pressure in the hydrogel over time,
    wherein the hydrogel is responsive to concentrations of both sugar and alcohol and is an unsubstituted hydrogel not modified to have substituents having particular affinities for sugar,
    wherein sugar exerts an osmotic effect on the hydrogel with increasing concentrations causing a reduction in pressure, and
    wherein alcohol entering the hydrogel causes an increase in pressure by expanding the hydrogel.

2. The method of claim 1 wherein the hydrogel is an hydroxyalkyl methacrylate.

3. The method of claim 1 wherein the holding of the hydrogel includes holding the hydrogel between a porous rigid support and a planar compressive member contacting a strain gauge, the hydrogel when wet exerting the base pressure against the compressive force of the planar compressive member, the solution traversing the porous rigid support to contact the hydrogel to thereby vary the force exerted via the planar compressive member on the strain gauge.

4. The method of claim 3 wherein the hydrogel is shaped to have a centrally thicker portion and to taper radially outwardly.

* * * * *